US012253530B2

(12) United States Patent
Thouvenot et al.

(10) Patent No.: US 12,253,530 B2
(45) Date of Patent: Mar. 18, 2025

(54) DIAGNOSIS METHOD OF MULTIPLE SCLEROSIS

(71) Applicants: CENTRE NATIONAL DE LA RECHERCHE SCIENTIFIQUE, Paris (FR); INSTITUT NATIONAL DE LA SANTE ET DE LA RECHERCHE MEDICAL (INSERM), Paris (FR); UNIVERSITE DE MONTPELLIER, Montpellier (FR); CENTRE HOSPITALIER UNIVERSITAIRE DE NÎMES, Nîmes (FR)

(72) Inventors: Eric Thouvenot, Saint-Gely-du-Fesc (FR); Philippe Marin, Saint-Gely-du-Fesc (FR); Serge Urbach, Juvignac (FR); Geoffrey Hinsinger, Montpellier (FR)

(73) Assignees: CENTRE NATIONAL DE LA RECHERCHE SCIENTIFIQUE, Paris (FR); INSTITUT NATIONAL DE LA SANTÉ ET DE LA RECHERCHE MÉDICAL (INSERM), Paris (FR); UNIVERSITE DE MONTPELLIER, Montpellier (FR); CENTRE HOSPITALIER UNIVERSITAIRE DE NÎMES, Nîmes (FR)

( * ) Notice: Subject to any disclaimer, the term of this patent is extended or adjusted under 35 U.S.C. 154(b) by 1151 days.

(21) Appl. No.: 17/057,269

(22) PCT Filed: May 22, 2019

(86) PCT No.: PCT/EP2019/063208
§ 371 (c)(1),
(2) Date: Nov. 20, 2020

(87) PCT Pub. No.: WO2019/224242
PCT Pub. Date: Nov. 28, 2019

(65) Prior Publication Data
US 2021/0364533 A1 Nov. 25, 2021

(30) Foreign Application Priority Data

May 22, 2018 (EP) ..................................... 18305630

(51) Int. Cl.
*G01N 33/68* (2006.01)
(52) U.S. Cl.
CPC . *G01N 33/6896* (2013.01); *G01N 2333/4722* (2013.01); *G01N 2333/70578* (2013.01);
(Continued)
(58) Field of Classification Search
None
See application file for complete search history.

(56) References Cited

U.S. PATENT DOCUMENTS

2003/0109420 A1* 6/2003 Valkirs .................. G01N 33/53
435/7.1
2004/0121343 A1* 6/2004 Buechler .............. C12Q 1/6883
435/6.14

FOREIGN PATENT DOCUMENTS

WO 2012/076722 A1 6/2012
WO 2015/023920 A1 2/2015
WO 2015/148389 A2 10/2015

OTHER PUBLICATIONS

Van der Vuurst de Vries, R. M., et al. "Soluble CD27 levels in cerebrospinal fluid as a prognostic biomarker in clinically isolated syndrome." JAMA neurology 74.3 (2017): 286-292. (Year: 2017).*
(Continued)

*Primary Examiner* — Rebecca M Giere
*Assistant Examiner* — Alexander Alexandrovic Volkov
(74) *Attorney, Agent, or Firm* — Maier & Maier, PLLC

(57) ABSTRACT

A method for diagnosing or prognosing, multiple sclerosis including the steps of (a) measuring the amount of at least one first protein as set forth in SEQ ID NO: 1, the at least first protein belonging to the group of proteins: a first protein, a second protein, a third protein, a fourth protein and a fifth protein, as set forth in SEQ ID NO 1 to 5, (b) comparing the amount of the at least first protein with the
(Continued)

amount of the same protein in a control sample, and (c) determining the status of the biological sample.

13 Claims, 8 Drawing Sheets

Specification includes a Sequence Listing.

(52) U.S. Cl.
CPC ... *G01N 2333/82* (2013.01); *G01N 2333/978* (2013.01); *G01N 2800/285* (2013.01)

(56) References Cited

OTHER PUBLICATIONS

Cepok, Sabine, et al. "Short-lived plasma blasts are the main B cell effector subset during the course of multiple sclerosis." Brain 128.7 (2005): 1667-1676. (Year: 2005).*

Pavelek, Zbyšek, et al. "Proteomic analysis of cerebrospinal fluid for relapsing-remitting multiple sclerosis and clinically isolated syndrome." Biomedical reports 5.1 (2016): 35-40. (Year: 2016).*
Marques, Fernanda, et al. "Lipocalin 2 is present in the EAE brain and is modulated by natalizumab." Frontiers in cellular neuroscience 6 (2012): 33. 1-10. (Year: 2012).*
Li, Gen, et al. "Inhibition of adenosine deaminase (ADA)-mediated metabolism of cordycepin by natural substances." Pharmacology research & perspectives 3.2 (2015): e00121. 1-11. (Year: 2015).*
International Search Report issued on Jul. 31, 2019 in corresponding International application No. PCT/EP2019/063208; 5 pages.
Ching-Ying Wu et al: "Serum level of circulating syndecan-1: A possible association with proliferative vasculopathy in systemic sclerosis", Journal of Dermatology., vol. 43, No. 1, Jun. 16, 2015 (Jun. 16, 2015), pp. 63-66.
Thouvenot Eric et al: "Cerebrospinal fluid chitinase-3-like protein 1 level is not an independent predictive factor for the risk of clinical conversion in radiologically isolated syndrome", Multiple Sclerosis Journal (MSJ), Sage Publications, Basingstoke, GB, Mar. 22, 2018 (Mar. 22, 2018), pp. 1-9.

* cited by examiner

Fig. 7

DIAGNOSIS METHOD OF MULTIPLE SCLEROSIS

FIELD

The invention relates to a diagnosis method of brain diseases, in particular of multiple sclerosis.

BACKGROUND

Multiple sclerosis (MS) is a potentially disabling disease of the brain and spinal cord (central nervous system).

In MS, the immune system attacks the protective sheath (myelin) that covers nerve fibers and causes communication problems between your brain and the rest of your body. Eventually, the disease can cause the nerves themselves to deteriorate or become permanently damaged.

Signs and symptoms of MS vary widely and depend on the amount of nerve damage and which nerves are affected. Some people with severe MS may lose the ability to walk independently or at all, while others may experience long periods of remission without any new symptoms.

There is no cure for multiple sclerosis. However, treatments can help speed recovery from attacks, modify the course of the disease and manage symptoms.

In order to anticipate the evolution of MS, it is necessary to rapidly determine if an individual is afflicted by MS or any correlative symptoms that may occur during the evolution of the pathology.

So there is a need in the art to provide a new efficient method to diagnose a MS in an individual and to propose a diagnosis of the outcome of the disease, i.e. a prognosis of the disease.

The invention intends to answer these needs.

SUMMARY

One aim of the invention is to provide a method that effectively and efficiently allow the practitioner to determine if a patient is afflicted by MS.

Another aim of the invention is to provide kit to rapidly carry out the method mentioned above.

Thus, the invention relates to a method for diagnosing and prognosing, in particular in vitro, multiple sclerosis in an individual suspected to be afflicted by multiple sclerosis, comprising the steps of:

a—Measuring, in a biological sample of said individual, the amount of at least one first protein, said at least one first protein comprising the amino acid sequence as set forth in SEQ ID NO: 1 (EGEAWLPEVEPGLTA), said at least first protein belonging to the group of proteins consisting of a first protein, a second protein, a third protein, a fourth protein and a fifth protein, said first protein comprising the amino acid sequence as set forth in SEQ ID NO: 1, said second protein comprising the amino acid sequence as set forth in SEQ ID NO: 2 (HCNSGLLV), said third protein comprising the amino acid sequence as set forth in SEQ ID NO: 3, (LLPVYELSGEHHDEEWSV), said fourth protein comprising the amino acid sequence as set forth in SEQ ID NO: 4, (SYPGLTSYLV), and said fifth protein comprising the amino acid sequence as set forth in SEQ ID NO: 5, (VDNALQSGNSQESVTEQDS)

b—comparing the amount of said at least first protein with the amount of the same protein in a control sample of the same nature originating from an individual not afflicted by MS, to establish a protein expression level ratio of said at least one protein, c—determining the status of said biological sample such that if the ratio established in step b) for said at least protein is higher than, or equal to, 2, said biological sample is representative of MS.

The invention is based on the surprising observation made by the inventors that the evaluation the expression level of SDC1 protein or gene is efficient to diagnose and to give a prognosis of MS in an individual.

Moreover, the invention is based on the fact that a minimal set of genes or of the corresponding proteins, including SDC1, can be studied to diagnose and to give a prognosis of MS in an individual.

The inventors demonstrate here that if an individual harbors, in a biological sample, an amount of SDC1 protein, or the corresponding mRNA, at least two fold higher compared to the expression level of SDC1 protein, or the corresponding mRNA, in a biological sample of the same nature originating from an healthy individual, said individual will be considered as afflicted, or will develop MS.

The list of the proteins used in the method according to the invention is summarized in the following table:

| | Name | Sequence | Corresponding sequence of a full length protein |
|---|---|---|---|
| SEQ ID NO: 1 | SDC1 | EGEAVVLPEVEPGLTA | SEQ ID NO: 6 |
| SEQ ID NO: 2 | CD27 | HCNSGLLV | SEQ ID NO: 7 |
| SEQ ID NO: 3 | CECR1 | LLPVYELSGEHHDEEWSV | SEQ ID NO: 8 |
| SEQ ID NO: 4 | NGAL | SYPGLTSYLV | SEQ ID NO: 9 |
| SEQ ID NO: 5 | IgKC | VDNALQSGNSQESVTEQDS | SEQ ID NO: 10 |

In the invention, it is necessary to measure the level of at least the protein SDC1 among the group of 5 proteins comprising SDC1, CD27, CECR1, NGAL and IgKC.

Thus, in the invention it is advantageous, in step a) of the method mentioned above to measure the amount of the protein of the list consisting of:

SDC1;
SDC1 and CD27;
SDC1 and CECR1;
SDC1 and NGAL;
SDC1 and IgKC;
SDC1, CD27 and CECR1;
SDC1, CD27 and NGAL;
SDC1, CD27 and IgKC;
SDC1, CECR1 and NGAL;
SDC1, CECR1 and IgKC;
SDC1, NGAL and IgKC;
SDC1, CD27, CECR1 and NGAL;
SDC1, CD27, CECR1 and IgKC;
SDC1, CECR1, NGAL and IgKC; and
SDC1, CD27, CECR1, NGAL and IgKC.

In the invention, the above proteins are quantified to determine their amount in order to compare this determined amount to the amount of the same protein originating from a control (healthy) sample. Common technics well known in the art can be used, such as immunological methods including western blot technics.

All the ratios are detailed in FIG. 7.

Advantageously, the invention relates to the method as mentioned above, wherein
step a) consists in measuring the amount of at least said first protein, said second protein and said third protein,
step b) consists in comparing the amount of said at least three proteins with the amount of the same proteins in a control sample of the same nature originating from an individual not afflicted by multiple sclerosis, to establish the respective protein expression level ratio for each of said at least three proteins, and
step c) consists of determining the status of said biological sample such that if the ratio established in step b)
for said at least first protein is higher than, or equal to, 2, i.e. the protein comprising the amino acid sequence as set forth in SEQ ID NO: 1;
for said at least second is higher than, or equal to, 2.5, i.e. the protein comprising the amino acid sequence as set forth in SEQ ID NO: 2; and
for said at least third protein is higher than, or equal to, 1.5, i.e. the protein comprising the amino acid sequence as set forth in SEQ ID NO: 3;
then, the biological sample is representative of a multiple sclerosis, in particular said biological sample is representative of a clinically isolated syndrome without conversion to multiple sclerosis, a clinically isolated syndrome with conversion to multiple sclerosis, a relapsing-remitting multiple sclerosis or a primary progressive multiple sclerosis.

The inventors advantageously also made the unexpected observation that the quantification of the amount of the SDC1, CD27 and CECR1 proteins, or the corresponding mRNAs, can be used to determine a cerebral disease of an individual.

When the expression level of the SDC1, CD27 and CECR1 proteins, in a determined biological sample originating from an individual is respectively equal to or higher than 2, 2.5 and 1.5, compared to the amount of the same proteins in a reference sample, said individual is considered to be afflicted by one of the following pathologies: multiple sclerosis, in particular clinically isolated syndrome without conversion to multiple sclerosis, a clinically isolated syndrome with conversion to multiple sclerosis, relapsing-remitting multiple sclerosis or primary progressive multiple sclerosis.

According to the invention, Clinically isolated syndrome (CIS) is a central nervous system demyelinating event isolated in time that is compatible with the possible future development of multiple sclerosis, or not.

In the invention, relapsing-remitting multiple sclerosis (RRMS) is the most common disease course of multiple sclerosis. This pathology is characterized by clearly defined attacks or new or increasing neurologic symptoms. These attacks—also called relapses or exacerbations—are followed by periods of partial or complete recovery (remissions). During remissions, all symptoms may disappear, or some symptoms may continue and become permanent. However, there is no apparent progression of the disease during the periods of remission. At different time points, RRMS can be further characterized as either active or not active, as well as worsening (a confirmed increase in disability over a specified period of time following a relapse) or not worsening. An increase in disability is confirmed when the person exhibits the same level of disability at the next scheduled neurological evaluation, typically 6 to 12 months later.

In the invention, primary progressive multiple sclerosis (PPMS) is characterized by worsening neurologic function (accumulation of disability) from the onset of symptoms, without any relapses or remissions. PPMS can be further characterized at different time points as either active (with an occasional relapse and/or evidence of new MRI activity) or not active, as well as with progression (evidence of disease worsening on an objective measure of change over time, with or without relapse or new MRI activity) or without progression. Approximately 15 percent of people with MS are diagnosed with PPMS.

Advantageously, the invention relates to the method as defined above, wherein step c) consists in determining the status of said biological sample such that if the ratio established in step b) for said third protein is higher than, or equal to, 3, then, the biological sample is representative of relapsing-remitting multiple sclerosis.

Advantageously, the invention relates to the method as defined above, wherein step c) consists in determining the status of said biological sample such that if the ratio established in step b) for said second protein is higher than, or equal to, 5, then, the biological sample is representative of MS, in particular clinically isolated syndrome with conversion to multiple sclerosis, relapsing-remitting multiple sclerosis or primary progressive multiple sclerosis.

Advantageously, the invention relates to the method as defined above, wherein said biological sample is a cerebrospinal fluid sample.

It is particularly advantageous to evaluate the amount of the protein defined above in cerebrospinal fluid (CSF) sample. The CSF is derived from blood plasma and is largely similar to it, except that CSF also contains proteins derived from the brain and can indicate pathological processes occurring in neurological diseases. Moreover, CSF is accessible by lumbar puncture, a technique largely used in neurological investigations given its minimally invasive character.

The invention also relates to a method for diagnosing, in particular in vitro, a central nervous system disease in an individual suspected to be afflicted by such a disease, said method comprising:
1. measuring the amount of at least one first protein, one second protein and one third protein, said first protein comprising the amino acid sequence as set forth in SEQ ID NO: 1, said second protein comprising the amino acid sequence as set forth in SEQ ID NO: 2, said third protein comprising the amino acid sequence as set forth in SEQ ID NO: 3, said at least one first protein, one second protein and one third protein belonging to the group of proteins consisting of a first protein, a second protein, a third protein, a fourth protein and a fifth protein, said first protein comprising the amino acid sequence as set forth in SEQ ID NO: 1, (EGEAWLPEVEPGLTA)

said second protein comprising the amino acid sequence as set forth in SEQ ID NO: 2 (HCNSGLLV), said third protein comprising the amino acid sequence as set forth in SEQ ID NO: 3, (LLPVYELSGEHHDEE-WSV)

said fourth protein comprising the amino acid sequence as set forth in SEQ ID NO: 4, (SYPGLTSYLV)

said fifth protein comprising the amino acid sequence as set forth in SEQ ID NO: 5, (VDNALQSGNSQESVTE-QDS)

1. comparing the amount of each of said at least one first protein, one second protein and one third protein with the amount of the same proteins in a biological sample of the same nature originating from an healthy individual not afflicted by a central nervous system disease, to establish the respective protein expression level ratios for each of said at least one first protein, one second protein and one third protein, and
2. determining the status of said biological sample such that if the ratio established in step b)
   a. for
      i. said at least first protein is higher than, or equal to, 2,
      ii. for said at least second is higher than, or equal to, 2.5, and
      iii. for said at least third protein is higher than, or equal to, 1.5 then the individual is afflicted by multiple sclerosis,
   1. for the second protein is higher than, or equal to, 2, then the individual is afflicted by multiple sclerosis or an inflammatory neurological disease
   2. for the third protein, is higher than, or equal to, 1.5, then the individual is afflicted by a clinically isolated syndrome without conversion to multiple sclerosis, a clinically isolated syndrome with conversion to multiple sclerosis, relapsing-remitting multiple sclerosis, primary progressive multiple sclerosis, an non inflammatory neurological disease, an inflammatory neurological disease or peripheral inflammatory neurological disease.

The method disclosed above allows a determination of a group of pathologies by the different expression levels of the first, the second and the third protein, respectively, SDC1, CD27 and CECR1.

When, compared to the amount in a biological sample of an healthy individual, the amount of SDC1 is higher than 2, the amount of CD27 is higher than 2.5 and the amount of CECR1 is higher than 1.5, then the individual from who derives the biological sample is afflicted by multiple sclerosis. When, compared to the amount in a biological sample of an healthy individual, the amount of CD27 is higher than 2, then the individual from who derives the biological sample is afflicted by multiple sclerosis or an inflammatory neurological disease. When, compared to the amount in a biological sample of an healthy individual, the amount of CECR1 is higher than 1.5, then the individual from who derives the biological sample is afflicted by multiple sclerosis, relapsing-remitting multiple sclerosis, primary progressive multiple sclerosis, an non inflammatory neurological disease, an inflammatory neurological disease or peripheral inflammatory neurological disease.

The use of the 3 proteins, and the evaluation of their amount, allows to discriminate different neural pathologies and to propose a differential diagnosis.

Advantageously, the invention relates to the method as defined above The method according to claim 5, said method comprising:

1. measuring the amount of the first protein, the second protein the third protein, the fourth protein and the fifth protein,
2. comparing the amount of the first protein, the second protein the third protein, the fourth protein and the fifth protein with the amount of the same proteins in a biological sample of the same nature originating from an healthy individual not afflicted by a central nervous system disease, to establish the respective protein expression level ratio for each of said at least four proteins, and
3. determining the status of said biological sample such that if the ratio established in step b)
4. for
   a. said at least first protein is higher than, or equal to, 2,
   b. for said at least second is higher than, or equal to, 2.5, and
   c. for said at least third protein is higher than, or equal to, 1.5 then the individual is afflicted by multiple sclerosis,
   1. for the third protein is higher than, or equal to, 2.5, then the individual is afflicted by multiple sclerosis, a non inflammatory neurological disease, an inflammatory neurological disease or peripheral inflammatory neurological disease, and
   2. for fourth protein is higher than, or equal to, 1.5, then the individual is afflicted by an inflammatory neurological disease.

In this advantageous embodiment, the quantification of the amount of a fourth protein, i.e. NGAL, allows to differentiate inflammatory neurological diseases from the other pathologies.

Advantageously, the invention relates to the method as defined above, wherein in step c. if the ratio established the third protein is higher than, or equal to 3 then the individual is afflicted by an inflammatory neurological disease, radiologically isolated syndrome with conversion to multiple sclerosis, a clinically isolated syndrome without conversion to multiple sclerosis, a clinically isolated syndrome with conversion to multiple sclerosis, relapsing-remitting multiple sclerosis or primary progressive multiple sclerosis.

Advantageously, the invention relates to the method as defined above, wherein in step c. if the ratio established the second protein is higher than, or equal to 5 then the individual is afflicted by a clinically isolated syndrome without conversion to multiple sclerosis, a clinically isolated syndrome with conversion to multiple sclerosis, relapsing-remitting multiple sclerosis or primary progressive multiple sclerosis.

More advantageously, the invention relates to the method as defined above, wherein said biological sample is a cerebrospinal fluid sample.

The invention also relates to a kit comprising a set of at least 3 antibodies liable to form a protein complex with at least one first protein, one second protein and one third protein, said first protein comprising the amino acid sequence as set forth in SEQ ID NO: 1, said second protein comprising the amino acid sequence as set forth in SEQ ID NO: 2, said third protein comprising the amino acid sequence as set forth in SEQ ID NO: 3, said at least one first protein, one second protein and one third protein belonging to the group of proteins consisting of a first protein, a second protein, a third protein, a fourth protein and a fifth protein, said first protein comprising the amino acid sequence as set forth in SEQ ID NO: 1, (EGEAWLPEVEPGLTA-SDC1), said second protein comprising the amino acid sequence as set forth in SEQ ID NO: 2 (HCNSGLLV-sDC27), said third protein comprising the amino acid sequence as set forth in SEQ ID NO: 3, (LLPVYELSGEHHDEE-WSV-CECR1)

said fourth protein comprising the amino acid sequence as set forth in SEQ ID NO: 4, (SYPGLTSYLV-NGAL)

said fifth protein comprising the amino acid sequence as set forth in SEQ ID NO: 5, (VDNALQSGNSQESVTE-QDS-IgKC).

The above kit contains at least 3 antibodies, each of at least 3 antibodies being able to form an immune complex with only one of said at least 3 proteins. In other words, the kit according to the invention contains at least one antibody that specifically recognizes at least one epitope of SDC1 protein, contains at least one antibody that specifically recognizes at least one epitope of CD27 protein, and contains at least one antibody that specifically recognizes at least one epitope of CECR1 protein. The skilled person knows that a specific antibody (i.e. that specifically recognizes an epitope) is not able to recognize another protein. Therefore, an anti-SDC1 antibody is not able to detect the presence, or interact with, either CD27 or CECR1.

Advantageously, the invention relates to the kit as mentioned above, each antibody being able to specifically form an immune complex with only one protein of said one first protein, one second protein and one third protein.

The invention also relates to the kit as defined above for its use for diagnosing a central nervous system disease.

Advantageously, the invention relates to the kit as defined above, for its use as defined above, wherein the central nervous system disease is multiple sclerosis.

The kit according to the invention can be used to diagnose cerebral disease, and advantageously to diagnose multiple sclerosis, in particular said biological sample is representative of a clinically isolated syndrome without conversion to multiple sclerosis, a clinically isolated syndrome with conversion to multiple sclerosis, relapsing-remitting multiple sclerosis or primary progressive multiple sclerosis.

In another aspect, the invention relates to a method for measuring the effect of a drug on the treatment or the outcome of MS, wherein said method comprising:

measuring in a biological sample originating from an individual treated with said drug the amount of at least a first protein, a second protein and a third protein, said first, second and third protein being respectively as set forth in SEQ ID NO: 1, SEQ ID NO: 2 and SEQ ID NO: 3, comparing the amount of said at least three proteins with the amount of the same proteins in a control sample of the same nature originating from an individual not afflicted by MS, to establish the respective protein expression level ratio for each of said at least three proteins, and determining the status of said biological sample such that if the ratio established above for said at least first protein is lower than 2, i.e. the protein comprising the amino acid sequence as set forth in SEQ ID NO: 1;

for said at least second is lower than 2.5, i.e. the protein comprising the amino acid sequence as set forth in SEQ ID NO: 2; and for said at least third protein is lower than 1.5, i.e. the protein comprising the amino acid sequence as set forth in SEQ ID NO: 3;

then, said drug had treated or had a positive effect on the outcome of the individual afflicted by a multiple sclerosis.

In this advantageous embodiment, the method according to the invention allows the pathologist to determine if a therapy had a positive effect on the development of MS in patients afflicted by a MS, or if said therapy can have an effect to limit or reduce the progression of the pathology.

Advantageous drugs are Rituximab, Ocrelizumab, Alemtuzumab and Cladribine, 4 therapies used in MS.

The invention will be better understood in the light of the following example and the 7 following figures.

BRIEF DESCRIPTION OF THE FIGURES

FIG. 2A represents high-resolution peptide profiling of CSF from symptomatic controls.

FIG. 2B represent high-resolution peptide profiling of CSF from RRMS.

FIG. 2C show up-regulation of CH13L1 and CH13L2 in RRMS, which was verified by ELISA.

Figure 7:
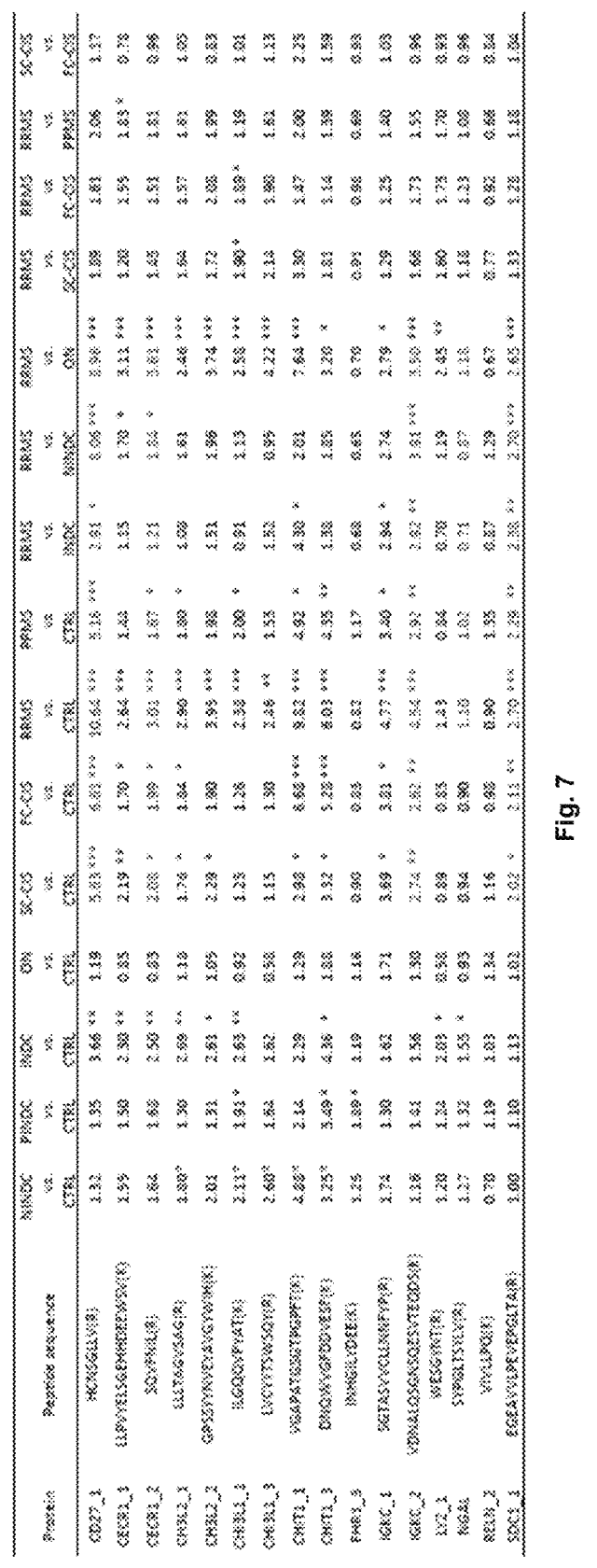

FIG. 7 is a table in which are shown the fold changes of 16 peptides selected for the verification step using PRM among the different group comparisons. Fold change significances (t-test p-values) obtained using Msstat add-on in Skyline software are shown. *: p-value<0.05; : p-value<0.001; *: p-value<0.0001. CTRL: control, INDC: inflammatory neurological disease, NINDC: non inflammatory neurological disease PINDC: peripheral inflammatory neurological disease, ON: isolated optic neuritis, RIS−: radiologically isolated syndrome without conversion to multiple sclerosis, RIS+: radiologically isolated syndrome with conversion to multiple sclerosis, CIS−: a clinically isolated syndrome without conversion to multiple sclerosis, CIS+: clinically isolated syndrome with conversion to multiple sclerosis, RRMS: relapsing-remitting multiple sclerosis and PPMS: primary progressive multiple sclerosis.

DETAILED DESCRIPTION

Example

Example: Combined Proteomic Analysis of Cerebrospinal Fluid from Multiple Sclerosis Patients and of Oligodendrocyte Secretomes for the Identification of New Multiple Sclerosis Biomarkers The general aim of our program is to combine different proteomic approaches to identify biomarkers of relapsing-remitting multiple sclerosis (RRMS) in cerebrospinal fluid (CSF). To achieve that goal, the inventors used complementary and sensitive quantitative proteomic approaches to:
1) analyze the effects of proinflammatory and proapoptotic treatments on the oligodendrocyte secretome;
2) compare CSF proteome of MS and control patients in order to identify candidate MS biomarkers;
3) verify a large set of candidate biomarkers in a new cohort comprising MS and control patients; and
4) validate a subset of biomarkers that passed the verification step on a large cohort comprising MS and control patients as well as patients with other inflammatory and non-inflammatory neurological diseases.

Step 1: Modifications of the Oligodendrocyte Secretome Upon Inflammation

Figure 1:
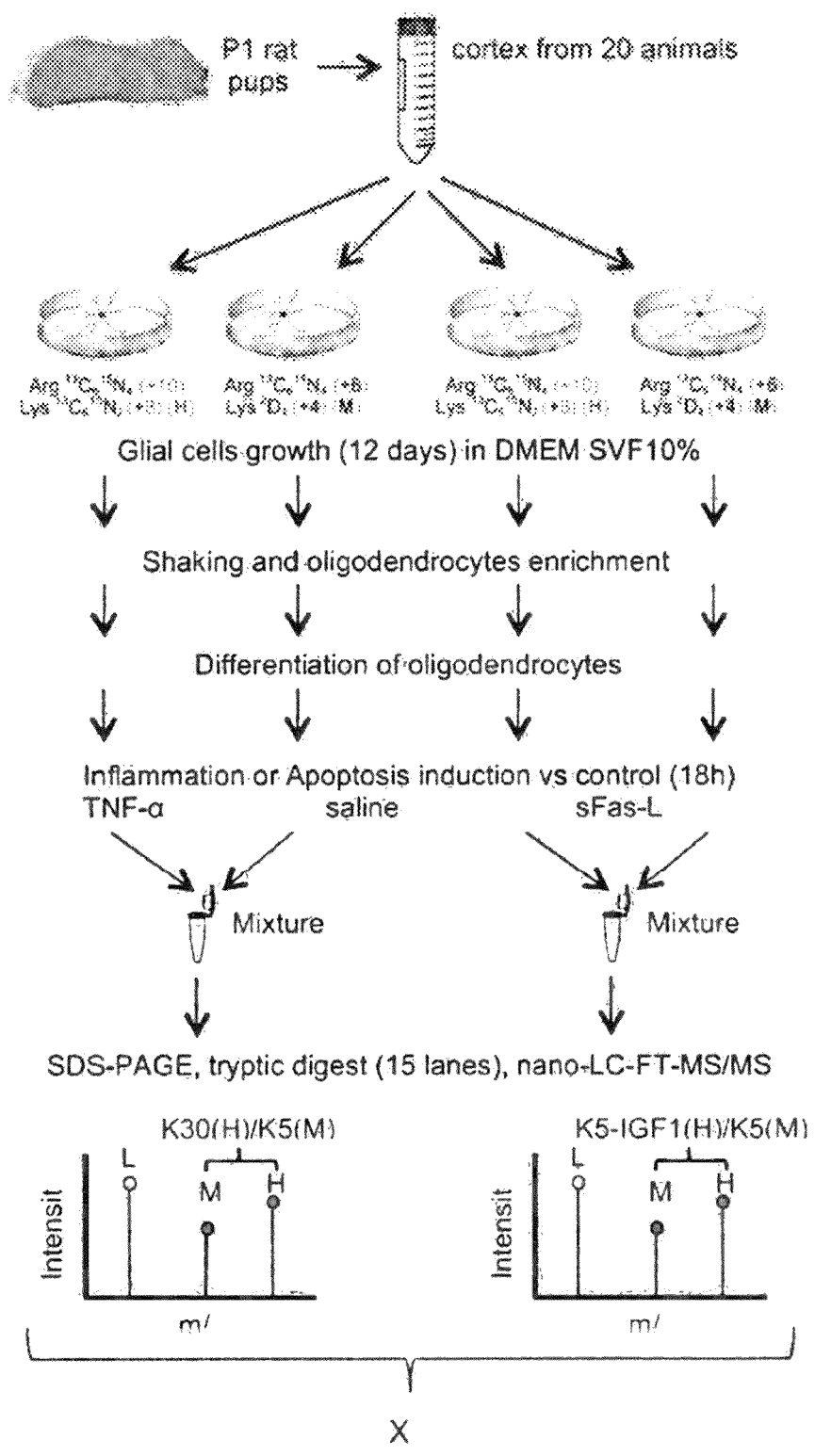
FIG. 1 is a schematic representation of the workflow proposed to study the variations in the oligodendrocyte secretome upon TNF-alpha or Fas-L treatment.

The effects of pro-inflammatory treatments on the secretome of murine oligodendrocytes were investigated using SILAC (stable isotope labeling by amino acids in cell culture). For this purpose, rat oligodendrocytes in primary culture were grown in a classic culture medium for 14 days, and then allowed to differentiate into oligodendrocytes in a SILAC culture medium containing two different types of stable isotope-labeled Lysine and Arginine and serum (FIG. 1). After 5 days of incorporation, each type of stable isotope labeled culture were incubated in a serum-free medium in the presence or in the absence of TNF-alpha in order to allow accumulation of secreted proteins. Supernatants from both conditions were harvested, mixed and analyzed using an Orbitrap Q-EXACTIVE™ mass spectrometer coupled to a nano-liquid chromatrography (Dionex Ultimate 3000). Protein ratios comparing the amount of proteins in supernatants of vehicle and TNF-alpha treated cells were determined using the MaxQuant software. The same experiments were replicated using Fas-ligand as an inducer of oligodendrocyte apoptosis, and compared with TNF-alpha-induced modification of oligodendrocyte seeretome (FIG. 2). Apoptosis was measured by differential counting of cells stained by propidium iodide (necrosis) and cells showing characteristic nuclear condensation and/or blebbing after Hoechst staining.

Altogether, 2,636 proteins were identified and quantified in secretome of rat oligodendrocytes exposed to either vehicle or TNF-alpha or Fas-L. Of these, 1,271 were quantified in all biological replicates performed for each experimental condition. Twelve of these proteins showed significantly different levels in the supernatant of oligodendrocytes treated with TNF-alpha and/or sFas-L, compared with vehicle (the following table represents significant changes in protein ratios in oligodendrocyte secretome upon inflammation and apoptosis).

| Accession number | Protein name | Treatment | Treatment/ vehicle Ratio |
|---|---|---|---|
| 063120 | Canalicular multispecific organic anion transporter 1 | TNF-a | 5.88 |
| P31721 | Complement C1q subcomponent subunit B | TNF-a | 2.09 |
| P31722 | Complement C1q subcomponent subunit C | sFas-L | 4.43 |
| P08025 | Insulin-like growth factor I | sFas-L | 0.25 |
| P24594 | Insulin-like growth factor-binding protein 5 | sFas-L | 0.05 |
| P24594 | Insulin-like growth factor-binding protein 5 | TNF-a | 0.03 |
| Q9JIL3-2 | Interleukin enhancer-binding factor 3 | sFas-L | 3.83 |
| P30152 | Neutrophil gelatinase-associated lipocalin (NGAL) | TNF-a | 6.72 |
| D3ZN61 | Leucine-rich repeat LGI family, member 3 | sFas L | 5.66 |
| D4A4M3 | Atrip protein | TNF-a | 0.26 |
| MORBFI | Complement C3 | TNF-a | 21.27 |
| D4A599 | Protein Dna hel 7 | TNF-a | 0.23 |
| F1MA59 | Collagen 4 A1 subunit | TNF-a | 0.31 |

Finally, this step provided a first comprehensive secretome map of murine oligodendrocytes and led to the identification of subtle changes in protein secretion upon pro-inflammatory and pro-apoptotic (above table), providing new insight into the physiology of these cells, targeted by auto-aggressive activated lymphocytes and macrophages in MS. It also identified a set of proteins exhibiting difference in secretion in response to a proinflammatory or a pro-apoptotic treatment. Some of them {C1qb, C1qc, C3, IGF1, IGFBP1, col4A1, NGAL} have already been described in human CSF and can be considered as potential CSF biomarkers of MS.

They were combined with candidate biomarkers arising from in depth CSF analysis of control and MS patients, for verification by targeted quantitative proteomics {PRM} in a new cohort using the Q-EXACTIVE™ instrument.

Step 2: High—Resolution Peptide Profiling of CSF.

Figure 2A:
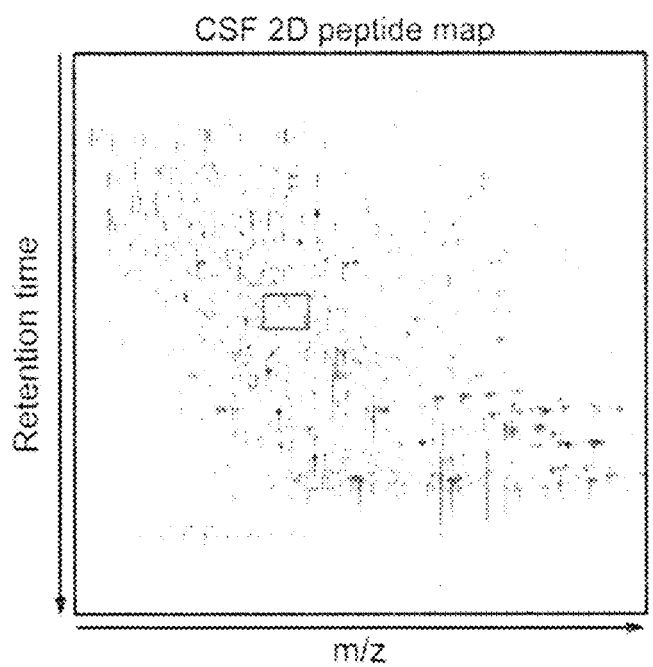
FIGS. 2A to 2C represent high-resolution peptide profiling of CSF from symptomatic controls and RRMS (2A and 2B) and show up-regulation of CH13L1 and CH13L2 in RRMS, which was verified by ELISA (2C).
Figure 2B:
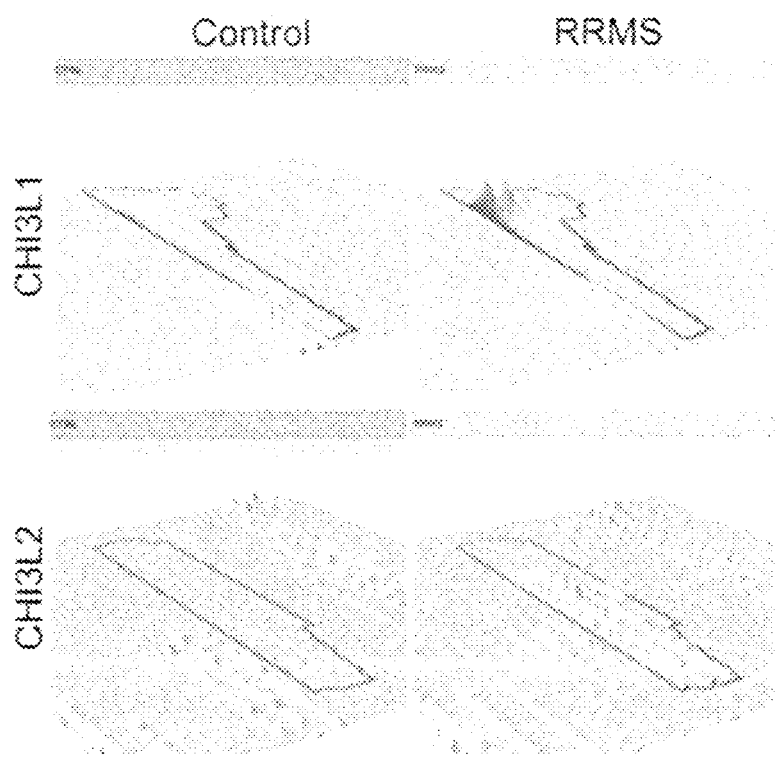
Figure 2C:
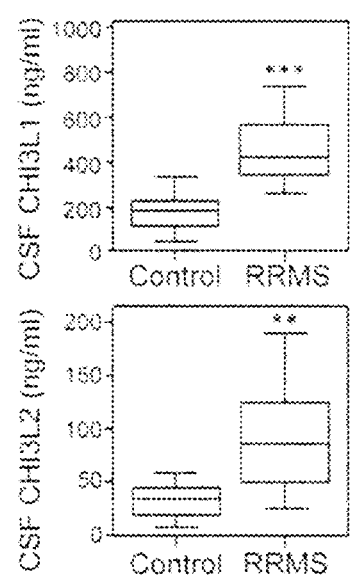

This step aimed at discovering new putative biomarkers of MS by direct analysis of CSF samples from MS patients and controls using high-resolution peptide profiling by nano-LC-FT-MS/MS in a LTQ Orbitrap Elite after immunodepletion of CSF samples of the 20 most abundant plasma proteins, using Proteoprep 20® columns (Sigma Aldrich) High-Resolution Peptide Profiling of CSF CSF samples from 10 MS vs. 10 control patients were immunodepleted using Proteoprep 20®, digested with trypsin on 3,000 Da filters and directly analyzed in a 180 minute gradient using a Quadrupole Orbitrap instrument (Q-EXACTIVE™, Thermo Scientific). The 20 peptide maps obtained without fractionation were matched with a reference map obtained after fractionation using MaxQuant and PROGENESIS® softwares (FIGS. 2A to 2C). Each new feature identified during the individual samples profiling were implemented in the reference peptide map.

The relative abundance of each peptide signature (and of the corresponding proteins) was quantified from the corresponding ion signals using PROGENESIS® LC-MS software (Nonlinear Dynamics). It allowed the detection of ~20,000 peptide features and the relative quantification of ~700 proteins, including ~20 proteins with significant difference in abundance in control and RRMS samples. These included two chitinase 3-like proteins, CHI3L1 and CH13L2 (FIG. 28, and the following table), whose up-regulation in CSF from RRMS patients was further verified by ELISA in a larger cohort (FIG. 3C).

| Uniprot | Protein names | Global Score |
|---------|---------------|--------------|
| P01625 | Len Ig kappa chain V-IV region | 4.5 |
| O15782-6 | Chitinase-3-like protein 2 | 4.5 |
| P01834 | Ig kappa chain e region | 4.5 |
| P36222 | Chitinase-3-like protein 1 | 4.5 |
| P04208 | WAH Ig lambda chain V-I region | 4.5 |
| B4E304 | Adenosine deaminase CECR1 | 4.5 |
| O9UJ14 | Gamma-glutamyltransferase 7 Ig heavy chain V-III region | 4.5 |
| P01766 | BRO | 4.5 |
| O08554-2 | Desmocollin-1 | 3.75 |
| O13231-3 | Chitotriosidase-1 | 3 |
| O14917-2 | Protocadherin-17 | 2.25 |
| P01011 | Alpha-1-antichymotrypsin | 2.25 |

The above table shows the statistical analysis of CSF label-free analysis comparing RRMS and control patients (12 significant proteins). Global scores are sums of different statistical scores used for analysis of quantitative proteomics data.

The same strategy was used to compare CSF samples from 10 CIS with rapid conversion to RRMS (less than 12 months) to other CIS patients and led to the identification of 6 putative biomarkers of conversion (following Table).

| UniProt | Protein names | Global Score |
|---------|---------------|--------------|
| O9BY79-2 | Membrane frizzled-related protein | 4.5 |
| P34059 | N-acetylgalactosamine-6-sulfatase | 3 |
| O92911 | Sodium/iodide cotransporter | 2.25 |
| P54802 | Alpha-N-acetylglucosaminidase | 2.25 |
| P12259 | Coagulation factor V | 1.75 |
| P80723 | Brain acid soluble protein 1 | 1.5 |

The above table shows the statistical analysis of CSF label-free analysis comparing CIS patients with rapid conversion to RRMS and other CIS patients (6 significant proteins). Global scores are sums of different statistical scores used for analysis of quantitative proteomics data.

In-depth proteomic analysis of the CSF from MS patients vs. controls and CIS patients provided one the most detailed CSF maps of MS patients and enriched databases for research in the field of MS as well as identified new candidate biomarkers for MS.

The combination of this approach with the proteomic analysis of in vitro inflamed oligodendrocytes furnished new candidates for verification by targeted quantitative proteomics.

Step 3: Selection and Verification of the Best Candidate MS Biomarkers.

Candidate biomarkers from both proteomic approaches, secretome analysis and CSF label-free proteomics, were combined for validation on a new cohort of MS and control patients by means of parallel reaction monitoring (PRM), using a quadrupole Orbitrap instrument (Q-EXACTIVE™).

Selection and verification of the best candidate MS biomarkers.

Results from both proteomic approaches were combined to increase the number of putative CSF biomarkers for validation on a large cohort of MS and control patients by means of PRM.

The inventors selected:

15 proteins (34 peptides) from the oligodendrocyte secretome;

18 proteins (49 peptides) from CSF analysis at the protein level;

39 proteins (106 peptides) from CSF analysis at the peptide level; and 15 proteins (37 peptides) from the literatures of PRM.

Altogether, they selected 226 peptides from 87 candidate proteins identified in CSF from MS patients, secretome of oligodendrocytes and from the literature. Heavy isotopes of N, O and C were used to produce 226 synthetic peptides (Thermo Fisher), with a mass difference of 10 Da compared to endogenous peptides. These peptides were spiked in an immunodepleted pool of CSF (100 microl) from MS and control patients. PRM analysis allowed detection of 224 of these peptides in CSF with a good sensitivity.

Figure 3:
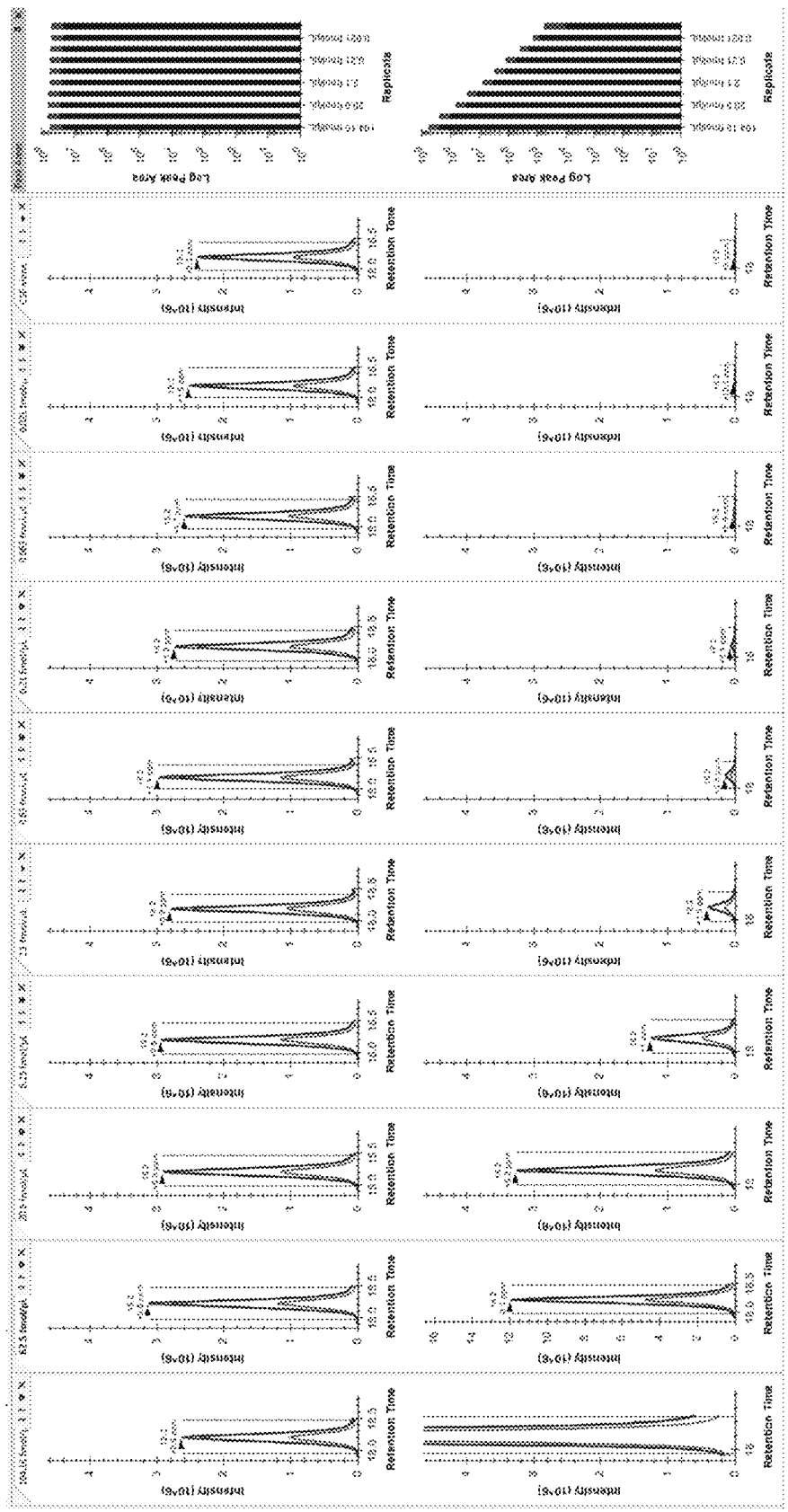
FIG. 3 represents determination of optimal labelled/endogenous peptide dilution for parallel reaction monitoring (PRM). A mixture of 1 microl of each synthetic (labelled) peptide was established. Serial dilutions (1/400 to 1/800.000) of the mixture were spiked in 10 aliquots of the same sample (CSF pool from 3 RRMS and 3 control patients). For each peptide, the labelled peptide intensity matching endogenous peptide intensity was determined (red circle). The corresponding dilution was used to build the final labelled peptides mixture for PRM analysis.
Figure 4:
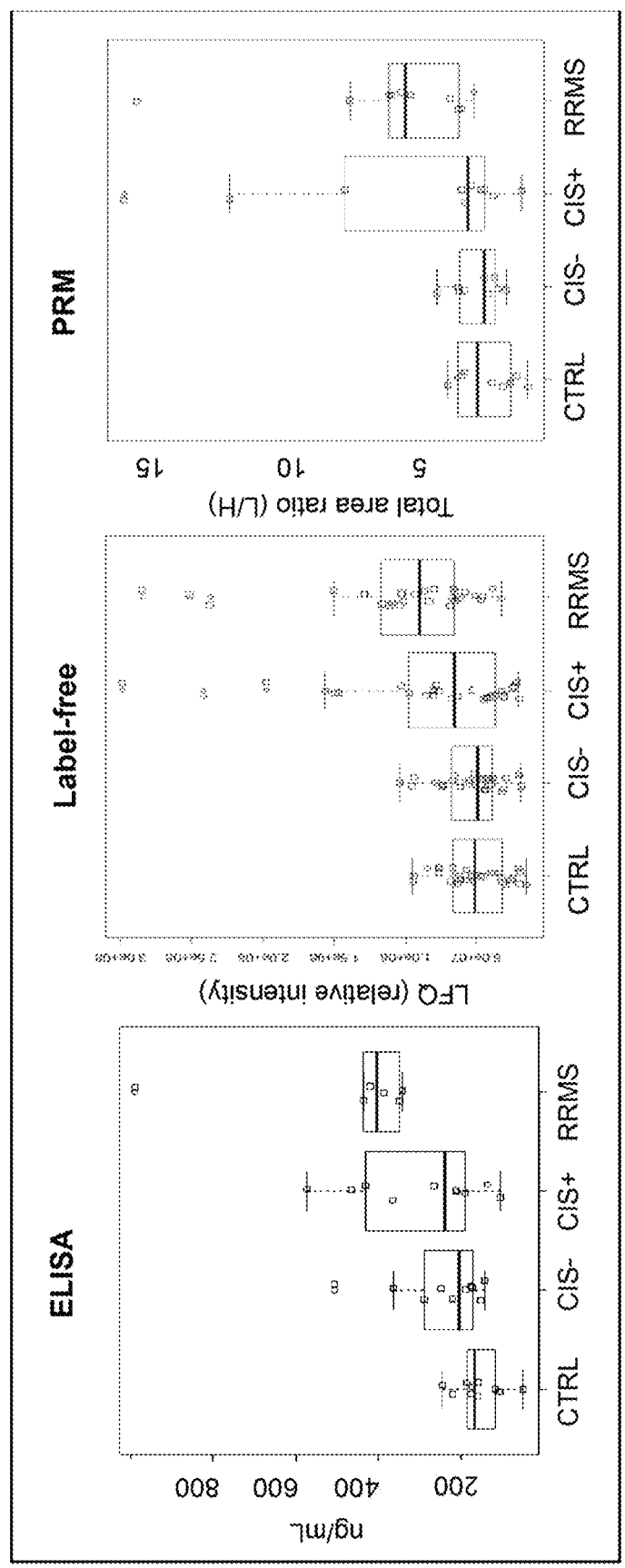
FIG. 4 represents a comparison of label-free and PRM peptide quantification with CSF concentration of the corresponding protein in different pathological conditions. CSF chitinase 3-like protein 1 (CH13L1) concentration was determined by ELISA (YKL-40, Microvue, Quidel Corp.) in four groups of 10 patients (CTRL: control; RRMS: relapsing remitting multiple sclerosis; CIS: clinically isolated syndrome). Relative intensity of peptide LVCYYTSWSQYR (SEQ ID NO: 13) was determined by label-free analysis in the same patients. Endogenous/labelled peptide ratio for LVCYYTSWSQYR (SEQ ID NO: 13) was also measured by parallel reaction monitoring (PRM) in each CSF sample. Similar expression profiles were observed among different methods, confirming the reliability of PRM method to quantify candidate biomarkers in CSF.

In order to increase the accuracy of endogenous/labelled peptide ratios, the inventors prepared a peptide mix corresponding to the concentration range of the native peptides in CSF (FIG. 3). Doing so, they were able to perform a relative quantification of each peptide in individual CSF samples from MS, CIS and control patients (FIG. 4).

Using optimal dilutions for 226 labelled peptides corresponding to the 87 selected proteins, the inventors analysed CSF samples from a new cohort of 60 patients using PRM: 10 controls (CTRL), 10 inflammatory neurological disease controls (INDC), 10 slow-converting clinically isolated syndromes (CIS−), 10 fast-converting clinically isolated syndromes (CIS), 10 relapsing-remitting multiple sclerosis (RRMS) and 10 primary progressive MS patients (PPMS).

Eleven proteins with significant RRMS/control or CIS+/CIS− ratios (p<0.05) and high absolute fold changes were chosen for validation (following table).

Figure 5:
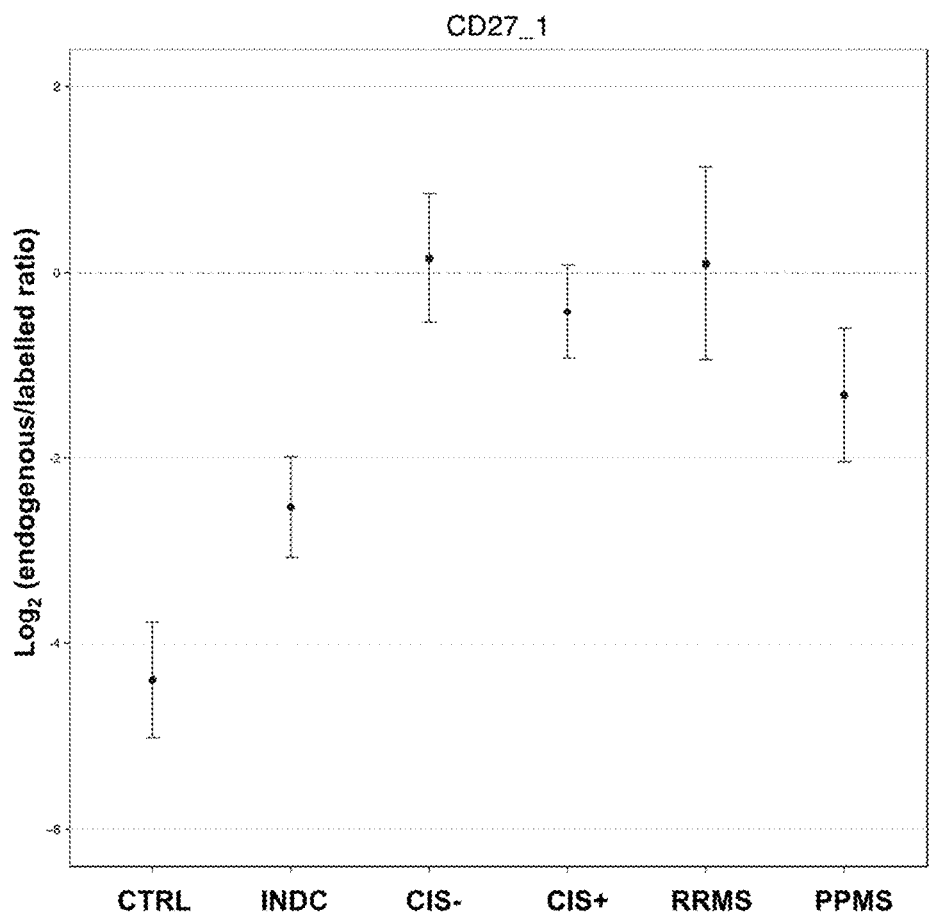
FIG. 5 represents an example of CSF biomarker verification by PRM (CD27 peptide 1).

Box-plots comparing the relative intensity of each peptide among the six clinical conditions analysed showed significant differences for a restricted set of candidates only (example for CD27, FIG. 5).

| PEPTIDE | RRMS/CTRL fold change | RRMS/CTRL p-value | RRMS/INDC fold change | RRMS/INDC p-value |
|---|---|---|---|---|
| CD27_1 | 22.47 | 0.0000 | 6.15 | 0.0008 |
| CECR1_1 | 3.59 | 0.0016 | 1.69 | 0.1865 |
| CECR1_2 | 1.81 | 0.0689 | 1.35 | 0.3500 |
| CH3L2_1 | 2.37 | 0.0177 | 1.51 | 0.2450 |
| CH3L2_2 | 2.97 | 0.0104 | 1.53 | 0.3131 |
| CHI3L1_1 | 1.88 | 0.0102 | 1.19 | 0.4685 |
| CHI3L1_3 | 1.96 | 0.0114 | 1.20 | 0.4780 |
| CHIT1_1 | 4.54 | 0.0095 | 1.64 | 0.3946 |
| CHIT1_3 | 6.41 | 0.0035 | 1.86 | 0.3248 |
| FHR1_3 | 0.56 | 0.0165 | 0.63 | 0.0566 |
| IgKC_1 | 3.56 | 0.0095 | 3.60 | 0.0089 |
| IgKC_2 | 3.81 | 0.0043 | 3.84 | 0.0041 |
| LYZ_1 | 1.92 | 0.0477 | 0.93 | 0.8215 |
| NGAL | 0.77 | 0.1630 | 0.67 | 0.0354 |
| RELN_2 | 0.51 | 0.0064 | 0.69 | 0.1149 |
| SDC1_1 | 2.59 | 0.0035 | 2.16 | 0.0161 |

The above table shows candidate biomarkers selected for validation by PRM. Altogether, 16 peptides corresponding to 11 proteins that showed best p-values and highest fold changes were selected. (CTRL: control; RRMS: relapsing-remitting multiple sclerosis; CIS: clinically isolated syndrome).

Finally, using PRM for verification of a set of 87 putative biomarkers of MS arising from a combination of label-free CSF analysis, oligodendrocyte secretome analysis and data from the literature provided a short list of 11 candidate biomarkers to be validated by PRM using highly purified synthetic peptides on a new and larger cohort of patients.

Step 4: Validation of a Restricted Set of MS Biomarkers that Passed the Verification Step.

Verification by parallel reaction monitoring (PRM) of a set of 87 putative biomarkers of multiple sclerosis (MS), arising from a combination of label-free cerebrospinal fluid (CSF) analysis, oligodendrocyte secretome analysis and data from the literature, provided a short list of 11 candidate biomarkers (16 peptides). Given the diversity of these candidate biomarkers and the lack of efficient and validated ELISA kit for most of them, the inventors decided to validate these putative MS biomarkers by a new PRM assay on a new and larger cohort (188 patients) including different control groups (symptomatic controls, inflammatory neurological disease controls, non inflammatory neurological disease controls, peripheral inflammatory neurological disease controls and isolated optic neuritis) and MS patients at different stages of the disease, including patients with radiologically isolated syndrome (RIS), clinically isolated syndrome (CIS), RRMS and PPMS (Table 5). RIS is defined by the presence demyelinating abnormalities suggestive of MS in a brain scan of patients with no symptoms of MS. This is considered as a presymptomatic form of MS. RIS− are defined as RIS patients without conversion to MS after more than 24 months of follow-up while RIS+ converted to MS during follow-up. In the same manner, CIS− are defined as CIS patients without conversion to MS after more than 24 months of follow-up while CIS+ converted to MS within 12 months of follow-up.

| Diagnostic | CTRL | NINDC | PINDC | INDC | ON | RIS | CIS | RRMS | PPMS |
|---|---|---|---|---|---|---|---|---|---|
| N | 30 | 13 | 13 | 13 | 15 | 30 | 30 | 30 | 14 |
| Age (mean, years) | 38.3 | 40.8 | 56.2 | 46.4 | 31.8 | 36.7 | 34.3 | 38.2 | 46.6 |
| Sex (female/total ratio) | 80% | 46% | 54% | 23% | 87% | 83% | 83% | 77% | 43% |
| CSF protein level (mean, g/L) | 0.36 | 0.33 | 0.41 | 0.39 | 036 | 0.39 | 0.34 | 0.39 | 0.51 |
| Presence of OCBs | 0% | 0% | 15% | 15% | 7% | 43% | 83% | 90% | 79% |
| Elevated IgG index | 0% | 0% | 0% | 0% | 0% | 27% | 60% | 78% | 58% |
| IgG index | 0.48 | 0.45 | 0.48 | 0.47 | 0.47 | ND | 0.86 | 1.12 | 0.84 |
| Positive CSF | 0% | 0% | 15% | 15% | 7% | 53% | 83% | 90% | 79% |
| DIS (Barkhof) | NA | NA | NA | NA | 0% | 50% | 60% | 80% | ND |
| DIS (Swanton) | NA | NA | NA | NA | 0% | 100% | 97% | 100% | ND |
| Gadolinium enhancement | NA | NA | NA | NA | 0% | 10% | 33% | 47% | ND |

The above table shows the patients of the second cohort used for validation of candidate biomarkers by PRM. (CTRL: symptomatic controls; INDC: inflammatory neurological disease controls; NINDC: non-inflammatory neurological disease controls; PINDC: peripheral inflammatory neurological disease controls; ON: isolated optic neuritis; RIS: radiologically isolated syndrome; CIS: clinically isolated syndrome; RRMS: relapsing-remitting MS; PPMS: primary progressive MS).

As for the verification step, CSF samples (100 µL) were immunodepleted of the 20 most abundant plasma proteins using the Proteoprep 20® immunodepletion column. A single depletion cycle was sufficient to accurately quantify the 16 target peptides corresponding to the 11 selected proteins, using purified, heavy isotope-labeled, synthetic peptides (AQUA ULTIMATE™, Thermo Fisher), as internal standards (following Table). For each peptide, limit of detection and limit of quantification were determined. Using optimal dilutions for these 16 labeled peptides, we thus quantified the native 16 peptides in CSF samples from a new cohort of 188 patients using PRM.

| Peptide | Sequence | Labelled residue | Mass change |
|---|---|---|---|
| CD27_1 | HCNSGLLV(R) (SEQ ID NO: 2) | Arginine (R) | +10 Da |
| CECR1_1 | LLPVYELSGEHHDEEWSV(K) (SEQ ID NO: 3) | Lysine (K) | +8 Da |
| CECR1_2 | SQVFNIL(R) (SEQ ID NO: 11) | Arginine (R) | +10 Da |
| CH3L2_1 | ILGQQVPYAT(K) (SEQ ID NO: 12) | Lysine (K) | +8 Da |
| CH3L2_2 | LVCYYTSWSQY(R) (SEQ ID NO: 13) | Arginine (R) | +10 Da |
| CHI3L1_1 | LLLTAGVSAG(R) (SEQ ID NO: 14) | Arginine (R) | +10 Da |
| CHI3L1_3 | GPSSYYNVEYAVGYWIH(K) (SEQ ID NO: 15) | Lysine (K) | +8 Da |
| CHIT1_1 | VGAPATGSGTPGPFT(K) (SEQ ID NO: 16) | Lysine (K) | +8 Da |
| CHIT1_3 | DNQWVGFDDVESF(K) (SEQ ID NO: 17) | Lysine (K) | +8 Da |
| FHR1_3 | NHGILYDEE(K) (SEQ ID NO: 18) | Lysine (K) | +8 Da |
| IgKC_1 | SGTASVVCLLNNFYP(R) (SAQ ID NO: 19) | Arginine (R) | +10 Da |
| IgKC_2 | VDNALQSGNSQESVTEQDS(K) (SEQ ID NO: 5) | Lysine (K) | +8 Da |
| LYZ_1 | WESGYNT(R) (SEQ ID NO: 20) | Arginine (R) | +10 Da |
| NGAL_1 | SYPGLTSYLV(R) (SEQ ID NO: 4) | Arginine (R) | +10 Da |
| RELN_2 | VIVLLPQ(K) SEQ ID NO: 21) | Lysine (K) | +8 Da |
| SDC1_1 | EGEAVVLPEVEPGLTA(R) (SEQ ID NO: 1) | Arginine (R) | +10 Da |

The above table shows the peptides quantified for biomarker validation by the second PRM round on the new cohort of 188 patients. Sixteen highly purified synthetic peptides (AQUA ULTIMATE™, Thermo Fisher) corresponding to 11 proteins were designed. Heavy isotopes of N, O and C were incorporated to provide a mass shift of 8 or 10 Da.

Figure 6:
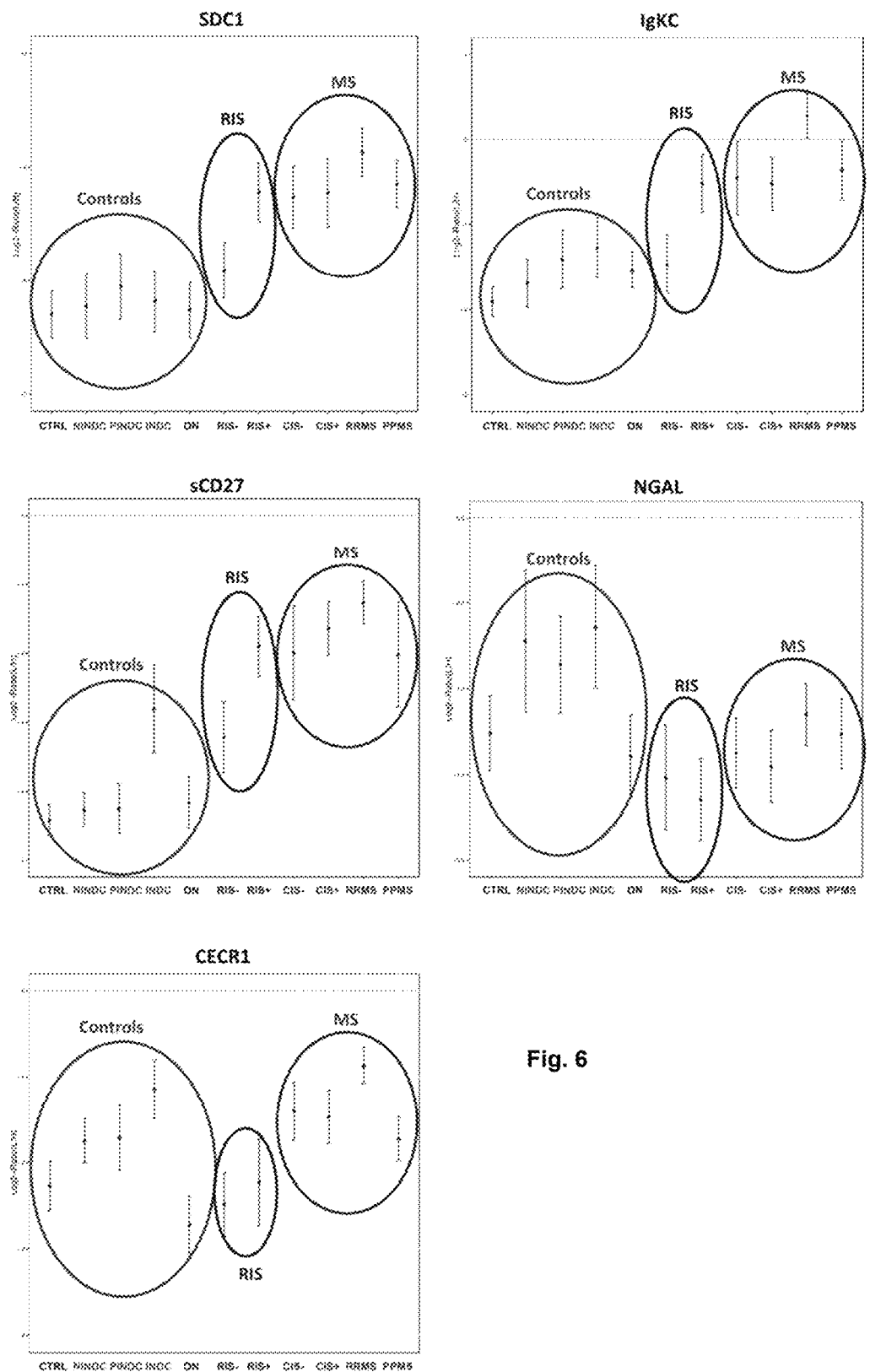
FIG. 6 represents expression profile of SDC1, IgKC, CD27, NGAL and CECR1 determined by PRM in different types of samples (CTRL: symptomatic controls; NOC: inflammatory neurological disease controls; NINDC: non inflammatory neurological disease controls; PINDC: peripheral inflammatory neurological disease controls; ON: isolated optic neuritis; RIS−: radiologically isolated syndrome without conversion to MS; RIS+: radiologically isolated syndrome with conversion to MS; CIS−: clinically isolated syndrome without conversion to MS; CIS+: clinically isolated syndrome with conversion to MS; RRMS: relapsing-remitting MS; PPMS: primary progressive MS).

Box-plots comparing the relative intensity of each peptide among the 11 clinical conditions analyzed were established. Comparison of the verification and the validation steps showed similar expression profiles among the different cohorts of patients (not shown), confirming the reliability of our PRM method to quantify candidate biomarkers in CSF. Especially, profiles of CH13L1, CH13L2 and CHIT1 were similar to previously published results obtained by the inventors' laboratory and other groups of investigators. The inventors also showed interesting differences for a restricted set of new candidate biomarkers of MS (FIG. 6). These include soluble Syndecan-1 (SDC1, sCD138), soluble CD27 (sCD27), immunoglobulin kappa chain C region (IgKC), Neutrophil gelatinase-associated lipocalin (NGAL, lipocalin-2) and Adenosine Deaminase (CECR1), which showed different and complementary profiles (FIG. 6):

Increase in all MS subtypes (CIS, RRMS, PPMS) but not in other CNS inflammatory conditions (SDC1, IgKC)
Discrimination between RIS− and RIS+ (SDC1, CD27, IgKC)
Increase in all CNS pathologies but not in MS (NGAL)
Increase in all CNS pathologies and in MS (CECR1)

These analyses also revealed that patients with an isolated optic neuritis (ON) share the same profile as symptomatic controls (CTRL), suggesting the absence of CSF inflammation, as observed in CIS patients with optic neuritis.

The combination of these biomarkers with complementary profiles could help deciphering:
1) positive diagnosis of MS whatever the stage of the disease (pre-symptomatic, after a first attack and later even in patients with primary progressive MS)
2) differential diagnosis with other inflammatory or non-inflammatory neurological diseases of the CNS or the peripheral nervous system
3) the risk of conversion to MS for patients with RIS, a presymptomatic form of MS.

Applications in Clinics:

The inventors wish to take advantage of these results to patent the combined use of these five biomarkers able to distinguish MS from other pathologies and predict evolution of RIS patients, even though this biomarker combination failed to predict conversion to MS after a CIS.

Indeed, all CIS patients included in this study were at high-risk of conversion to MS according to the presence of several demyelinating lesions on first MRI (Swanton criteria).

Moreover, the study provided a more extensive validation (on a larger set of patients and pathologies), compared to previously identified candidate biomarkers, except for CH13L1.

Further validation using ELISA will be performed to confirm these results and build a biological test for routine characterization of patients with potential CNS inflammatory diseases, even before the occurrence of neurological symptoms. The discovery of these new MS biomarkers in CSF could be useful for developing future diagnostic tools as well as new therapies.

Finally, this combination of biomarkers also revealed different pathways possibly involved in MS and that may constitute therapeutic targets for the management of the disease. In particular, CD27, SDC1 and CECR1 are expressed by lymphocytes targeted by several immunotherapies (anti-CD52 (alemtuzumab), anti-CD20 (rituximab, ocrelizumab), and cladribine). Translation to serum will also offer the possibility to facilitate monitoring of the activity of the disease and the response to different immunomodulatory or immunosuppressive treatments.

In conclusion, the inventors' proteomics studies of an in vitro cellular model reproducing some features of the disease (primary cultures of oligodendrocytes exposed to pro-inflammatory/pro-apoptotic treatments) and of CSF samples of patients with MS and other disease controls, identified new biomarkers relevant for MS diagnosis and prognosis.

The invention claimed is:

1. A method for diagnosing multiple sclerosis in an individual suspected to be afflicted by multiple sclerosis, comprising the steps of:
   a) measuring, in a biological sample of said individual, the amount of at least one first protein, said at least one first protein comprising the amino acid sequence as set forth in SEQ ID NO: 1, said at least one first protein belonging to the group of proteins consisting of a first protein, a second protein, a third protein, a fourth protein and a fifth protein,
   said first protein comprising the amino acid sequence as set forth in SEQ ID NO: 1,
   said second protein comprising the amino acid sequence as set forth in SEQ ID NO: 2,
   said third protein comprising the amino acid sequence as set forth in SEQ ID NO: 3,
   said fourth protein comprising the amino acid sequence as set forth in SEQ ID NO: 4, and
   said fifth protein comprising the amino acid sequence as set forth in SEQ ID NO: 5,
   b) comparing the amount of said at least one first protein with the amount of the same protein in a control sample of the same nature originating from a healthy individual not afflicted by multiple sclerosis, to establish a protein expression level ratio of said at least one first protein,
   c) diagnosing said individual as having multiple sclerosis for the ratio established in step b) for said at least one first protein is higher than, or equal to, 2.

2. The method according to claim 1, wherein step a) consists of measuring the amount of at least said first protein, said second protein and said third protein, step b) consists of comparing the amount of said at least three proteins with the amount of the same proteins in a control sample of the same nature originating from a healthy individual not afflicted by multiple sclerosis, to establish the respective protein expression level ratio for each of said at least three proteins, and step c) consists of diagnosing said individual as having multiple sclerosis for the ratio established in step b)

for said at least first protein is higher than, or equal to, 2, for said at least second protein is higher than, or equal to, 2.5, and for said at least third protein is higher than, or equal to, 1.5.

3. The method according to claim 2, wherein said individual is diagnosed as having relapsing-remitting multiple sclerosis in step c) for the ratio established in step b)

for said at least first protein is higher than, or equal to, 2, for said at least second protein is higher than, or equal to, 2.5, and for said at least third protein is higher than, or equal to 3.

4. The method according to claim 2, wherein said individual is diagnosed as having multiple sclerosis in step c) for the ratio established in step b)

for said at least first protein is higher than, or equal to, 2, for said at least second protein is higher than, or equal to 5, for said at least third protein is higher than, or equal to, 1.5.

5. The method according to claim 1, wherein said biological sample is a cerebrospinal fluid sample.

6. A method for diagnosing in vitro a central nervous system disease in an individual suspected to be afflicted by such a disease, said method comprising:

a) measuring the amount of at least one first protein, one second protein and one third protein, said first protein comprising the amino acid sequence as set forth in SEQ ID NO: 1, said second protein comprising the amino acid sequence as set forth in SEQ ID NO: 2, said third protein comprising the amino acid sequence as set forth in SEQ ID NO: 3, said at least one first protein, one second protein and one third protein belonging to the group of proteins consisting of a first protein, a second protein, a third protein, a fourth protein and a fifth protein, said first protein comprising the amino acid sequence as set forth in SEQ ID NO: 1, said second protein comprising the amino acid sequence as set forth in SEQ ID NO: 2, said third protein comprising the amino acid sequence as set forth in SEQ ID NO: 3, said fourth protein comprising the amino acid sequence as set forth in SEQ ID NO: 4, said fifth protein comprising the amino acid sequence as set forth in SEQ ID NO: 5, b) comparing the amount of each of said at least one first protein, one second protein and one third protein with the amount of the same proteins in a biological sample of the same nature originating from a healthy individual not afflicted by a central nervous system disease, to establish the respective protein expression level ratios for each of said at least one first protein, one second protein and one third protein, and c) diagnosing said individual as having:

(i) multiple sclerosis for the ratios of established in step b):

(1) for said at least first protein is higher than, or equal to, 2, (2) for said at least second protein is higher than, or equal to, 2.5, and (3) for said at least third protein is higher than, or equal to, 1.5, (ii) multiple sclerosis or an inflammatory neurological disease for the ratio established in step b) for said at least the second protein is higher than, or equal to, 2; or (iii) a clinically isolated syndrome without conversion to multiple sclerosis, a clinically isolated syndrome with conversion to multiple sclerosis, relapsing-remitting multiple sclerosis, primary progressive multiple sclerosis, a non inflammatory neurological disease, an inflammatory neurological disease or peripheral inflammatory neurological disease for the ration established in step b) for said at least third protein is higher than, or equal to, 1.5.

7. The method according to claim 6, said method comprising:

a) measuring the amount of the first protein, the second protein, the third protein, the fourth protein and the fifth protein, b) comparing the amount of the first protein, the second protein the third protein, the fourth protein and the fifth protein with the amount of the same proteins in a biological sample of the same nature originating from a healthy individual not afflicted by a central nervous system disease, to establish the respective protein expression level ratio for each of the first protein, the second protein, the third protein, the fourth protein and the fifth protein, and c) diagnosing said individual as having:

(iv) multiple sclerosis for the ratio established in step b) for each of the first protein, the second protein, the third protein, the fourth protein and the fifth protein is higher than, or equal to, 2, (v) multiple sclerosis or an inflammatory neurological disease for the ratio established in step b) for the second protein, is higher than, or equal to, 2.5, (vi) multiple sclerosis, a non inflammatory neurological disease, an inflammatory neurological disease or peripheral inflammatory neurological disease for the ratio established in step b) for the third protein is higher than, or equal to, 1.5, and (vii) an inflammatory neurological disease for the ratio established in step b) for the fourth protein is higher than, or equal to, 1.5.

8. The method according to claim 6, wherein in step c) diagnosing said individual as having an inflammatory neurological disease radiologically isolated syndrome with conversion to multiple sclerosis, a clinically isolated syndrome without conversion to multiple sclerosis, a clinically isolated syndrome with conversion to multiple sclerosis, relapsing-remitting multiple sclerosis or primary progressive multiple sclerosis for the ratio established for the third protein is higher than, or equal to, 3.

9. The method according to claim 6, wherein in step c) diagnosing said individual as having multiple sclerosis for the ratio established for the second protein is higher than, or equal to, 5.

10. The method according to claim 6, wherein said biological sample is a cerebrospinal fluid sample.

11. A kit comprising a set of at least 3 antibodies liable to form a protein complex with at least one first protein, one second protein and one third protein,
   said first protein comprising the amino acid sequence as set forth in SEQ ID NO: 1,
   said second protein comprising the amino acid sequence as set forth in SEQ ID NO: 2,
   said third protein comprising the amino acid sequence as set forth in SEQ ID NO: 3,
   said at least one first protein, one second protein and one third protein belonging to the group of proteins consisting of a first protein, a second protein, a third protein, a fourth protein and a fifth protein,
   said first protein comprising the amino acid sequence as set forth in SEQ ID NO: 1,
   said second protein comprising the amino acid sequence as set forth in SEQ ID NO: 2,
   said third protein comprising the amino acid sequence as set forth in SEQ ID NO: 3,
   said fourth protein comprising the amino acid sequence as set forth in SEQ ID NO: 4,
   said fifth protein comprising the amino acid sequence as set forth in SEQ ID NO: 5.

12. The kit according to claim 11, comprising at least 3 antibodies, each antibody being able to specifically form an immune complex with only one protein of said one first protein, one second protein and one third protein.

13. The method according to claim 2, wherein said individual is diagnosed as having clinically isolated syndrome without conversion to multiple sclerosis, a clinically isolated syndrome with conversion to multiple sclerosis, relapsing-remitting multiple sclerosis or primary progressive multiple sclerosis.

* * * * *

```
                       SEQUENCE LISTING

<160> NUMBER OF SEQ ID NOS: 21

<210> SEQ ID NO 1
<211> LENGTH: 16
<212> TYPE: PRT
<213> ORGANISM: Artificial Sequence
<220> FEATURE:
<223> OTHER INFORMATION: deriverd from hSDC1

<400> SEQUENCE: 1

Glu Gly Glu Ala Val Val Leu Pro Glu Val Glu Pro Gly Leu Thr Ala
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: derived from hsDC27

<400> SEQUENCE: 2

His Cys Asn Ser Gly Leu Leu Val
1               5

<210> SEQ ID NO 3
<211> LENGTH: 18
<212> TYPE: PRT
<213> ORGANISM: Artificial Sequence
<220> FEATURE:
<223> OTHER INFORMATION: derived from hCECR1

<400> SEQUENCE: 3

Leu Leu Pro Val Tyr Glu Leu Ser Gly Glu His His Asp Glu Glu Trp
1               5                   10                  15

Ser Val

<210> SEQ ID NO 4
<211> LENGTH: 10
<212> TYPE: PRT
<213> ORGANISM: Artificial Sequence
<220> FEATURE:
<223> OTHER INFORMATION: derived from hNGAL

<400> SEQUENCE: 4

Ser Tyr Pro Gly Leu Thr Ser Tyr Leu Val
1               5                   10

<210> SEQ ID NO 5
<211> LENGTH: 19
<212> TYPE: PRT
<213> ORGANISM: Artificial Sequence
```

```
<220> FEATURE:
<223> OTHER INFORMATION: derived from hIGKC

<400> SEQUENCE: 5

Val Asp Asn Ala Leu Gln Ser Gly Asn Ser Gln Glu Ser Val Thr Glu
1               5                   10                  15

Gln Asp Ser

<210> SEQ ID NO 6
<211> LENGTH: 334
<212> TYPE: PRT
<213> ORGANISM: Homo sapiens

<400> SEQUENCE: 6

Met Gln Gln Arg Leu Val Gly Ser Lys Cys Gln Cys Leu Ala Pro Ser
1               5                   10                  15

Leu Pro His Leu Glu Leu Ser Leu Gly Gly Gly Ala Ala Gly Glu
                20                  25                  30

Gly Arg Ala Glu Ser Leu Asp Glu Ser Glu Ala Met Ile Pro Gln Ile
            35                  40                  45

Val Ala Thr Asn Leu Pro Pro Glu Asp Gln Asp Gly Ser Gly Asp Asp
50                  55                  60

Ser Asp Asn Phe Ser Gly Ser Gly Ala Gly Ala Leu Gln Asp Ile Thr
65                  70                  75                  80

Leu Ser Gln Gln Thr Pro Ser Thr Trp Lys Asp Thr Gln Leu Leu Thr
                85                  90                  95

Ala Ile Pro Thr Ser Pro Glu Pro Thr Gly Leu Glu Ala Thr Ala Ala
            100                 105                 110

Ser Thr Ser Thr Leu Pro Ala Gly Glu Gly Pro Lys Glu Gly Glu Ala
        115                 120                 125

Val Val Leu Pro Glu Val Glu Pro Gly Leu Thr Ala Arg Glu Gln Glu
130                 135                 140

Ala Thr Pro Arg Pro Arg Glu Thr Thr Gln Leu Pro Thr Thr His Leu
145                 150                 155                 160

Ala Ser Thr Thr Thr Ala Thr Thr Ala Gln Glu Pro Ala Thr Ser His
                165                 170                 175

Pro His Arg Asp Met Gln Pro Gly His His Glu Thr Ser Thr Pro Ala
            180                 185                 190

Gly Pro Ser Gln Ala Asp Leu His Thr Pro His Thr Glu Asp Gly Gly
        195                 200                 205

Pro Ser Ala Thr Glu Arg Ala Ala Glu Asp Gly Ala Ser Ser Gln Leu
    210                 215                 220

Pro Ala Ala Glu Gly Ser Gly Glu Gln Asp Phe Thr Phe Glu Thr Ser
225                 230                 235                 240

Gly Glu Asn Thr Ala Val Val Ala Val Glu Pro Asp Arg Arg Asn Gln
                245                 250                 255

Ser Pro Val Asp Gln Gly Ala Thr Gly Ala Ser Gln Gly Leu Leu Asp
            260                 265                 270

Arg Lys Glu Val Leu Gly Gly Val Ile Ala Gly Gly Leu Val Gly Leu
        275                 280                 285

Ile Phe Ala Val Cys Leu Val Gly Phe Met Leu Tyr Arg Met Lys Lys
    290                 295                 300

Lys Asp Glu Gly Ser Tyr Ser Leu Glu Glu Pro Lys Gln Ala Asn Gly
305                 310                 315                 320

Gly Ala Tyr Gln Lys Pro Thr Lys Gln Glu Glu Phe Tyr Ala
```

325                 330

<210> SEQ ID NO 7
<211> LENGTH: 405
<212> TYPE: PRT
<213> ORGANISM: Homo sapiens

<400> SEQUENCE: 7

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Lys Arg Gln Asn
    210                 215                 220

Thr Gly Leu Arg Ser Cys Pro Cys Thr Thr Pro His Trp Leu Asn Ser
225                 230                 235                 240

Thr Ala His Ala Trp Asn Leu Thr Glu Thr His Gln Leu His Phe Thr
                245                 250                 255

Ser Leu Gly Pro Thr Pro Ser Leu Pro Leu Ala Gly Val Leu Leu Thr
            260                 265                 270

Pro Leu Pro Gln Gly His Pro Pro Leu Pro Ile Ser Phe Ser Arg Leu
        275                 280                 285

Pro Leu Pro Pro Leu Leu Ala Lys Thr His Arg Ile Ser Phe Cys Arg
    290                 295                 300

Gln Arg Arg Lys Ser Cys Gly Ala Cys Arg Ala Leu Ser Leu Gln Leu
305                 310                 315                 320

Pro Gln Gly Gly Gly Gly Gln His His Pro His Pro Gly Gly Leu Pro
                325                 330                 335

Lys Thr Gly Ala Cys Leu Leu Pro Leu Ser Gln His Leu Arg Glu Leu
            340                 345                 350

His Tyr Ser Pro Gly Leu His Pro His Pro Ala Asp His Pro Arg Glu
        355                 360                 365

-continued

```
Ser Glu Thr Trp Gln Pro Gln Leu Gln Ser His Pro Leu Val Arg Ala
    370                 375                 380

Leu Ser Cys Val His Val Thr Glu Cys Leu Phe Glu Thr Gly Arg Asp
385                 390                 395                 400

Glu Asp Lys Tyr Gly
                405

<210> SEQ ID NO 8
<211> LENGTH: 511
<212> TYPE: PRT
<213> ORGANISM: Homo sapiens

<400> SEQUENCE: 8

Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Leu Lys Glu Lys Met Met Arg Leu Gly Gly
        35                  40                  45

Arg Leu Val Leu Asn Thr Lys Glu Glu Leu Ala Asn Glu Arg Leu Met
    50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
                85                  90                  95

Gln Val Phe Asn Ile Leu Arg Met Met Pro Lys Gly Ala Ala Leu His
            100                 105                 110

Leu His Asp Ile Gly Ile Val Thr Met Asp Trp Leu Val Arg Asn Val
        115                 120                 125

Thr Tyr Arg Pro His Cys His Ile Cys Phe Thr Pro Arg Gly Ile Met
    130                 135                 140

Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Asn Val Thr
                165                 170                 175

Glu Phe Asp Asp Ser Leu Leu Arg Asn Phe Thr Leu Val Thr Gln His
            180                 185                 190

Pro Glu Val Ile Tyr Thr Asn Gln Asn Val Val Trp Ser Lys Phe Glu
        195                 200                 205

Thr Ile Phe Phe Thr Ile Ser Gly Leu Ile His Tyr Ala Pro Val Phe
    210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
                245                 250                 255

Gly Glu His His Asp Glu Glu Trp Ser Val Lys Thr Tyr Gln Glu Val
            260                 265                 270

Ala Gln Lys Phe Val Glu Thr His Pro Glu Phe Ile Gly Ile Lys Ile
        275                 280                 285

Ile Tyr Ser Asp His Arg Ser Lys Asp Val Ala Val Ile Ala Glu Ser
    290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu Arg Asp
                325                 330                 335
```

Tyr Lys Glu Ala Leu Met Ile Pro Ala Lys Asp Gly Val Lys Leu Pro
                340                 345                 350

Tyr Phe Phe His Ala Gly Glu Thr Asp Trp Gln Gly Thr Ser Ile Asp
            355                 360                 365

Arg Asn Ile Leu Asp Ala Leu Met Leu Asn Thr Thr Arg Ile Gly His
        370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
                405                 410                 415

Leu Val Ser Asp Leu Arg Asn His Pro Val Ala Thr Leu Met Ala Thr
            420                 425                 430

Gly His Pro Met Val Ile Ser Ser Asp Asp Pro Ala Met Phe Gly Ala
        435                 440                 445

Lys Gly Leu Ser Tyr Asp Phe Tyr Glu Val Phe Met Gly Ile Gly Gly
            450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
                485                 490                 495

Trp Lys Lys Arg Trp Asp Lys Phe Ile Ala Asp Val Ala Thr Lys
            500                 505                 510

<210> SEQ ID NO 9
<211> LENGTH: 247
<212> TYPE: PRT
<213> ORGANISM: Homo sapiens

<400> SEQUENCE: 9

Met Thr Ala Leu Pro Ala His Arg Pro Pro Ala His Ile Gln Gly Asn
1               5                   10                  15

Gln Lys Lys Glu Thr Ala Gln Gly Arg His Arg Gly Ser Arg Cys Pro
            20                  25                  30

Cys Gln Arg Pro Ser Ser His His Ser Ala Cys Phe Leu Gly Pro Glu
        35                  40                  45

Ile Met Pro Leu Gly Leu Leu Trp Leu Gly Leu Ala Leu Leu Gly Ala
    50                  55                  60

Leu His Ala Gln Ala Gln Asp Ser Thr Ser Asp Leu Ile Pro Ala Pro
65                  70                  75                  80

Pro Leu Ser Lys Val Pro Leu Gln Gln Asn Phe Gln Asp Asn Gln Phe
                85                  90                  95

Gln Gly Lys Trp Tyr Val Val Gly Leu Ala Gly Asn Ala Ile Leu Arg
            100                 105                 110

Glu Asp Lys Asp Pro Gln Lys Met Tyr Ala Thr Ile Tyr Glu Leu Lys
        115                 120                 125

Glu Asp Lys Ser Tyr Asn Val Thr Ser Val Leu Phe Arg Lys Lys Lys
    130                 135                 140

Cys Asp Tyr Trp Ile Arg Thr Phe Val Pro Gly Cys Gln Pro Gly Glu
145                 150                 155                 160

Phe Thr Leu Gly Asn Ile Lys Ser Tyr Pro Gly Leu Thr Ser Tyr Leu
                165                 170                 175

Val Arg Val Val Ser Thr Asn Tyr Asn Gln His Ala Met Val Phe Phe
            180                 185                 190

Lys Lys Val Ser Gln Asn Arg Glu Tyr Phe Lys Ile Thr Leu Tyr Gly

```
                195                 200                 205
Arg Thr Lys Glu Leu Thr Ser Glu Leu Lys Glu Asn Phe Ile Arg Phe
210                 215                 220

Ser Lys Ser Leu Gly Leu Pro Glu Asn His Ile Val Phe Pro Val Pro
225                 230                 235                 240

Ile Asp Gln Cys Ile Asp Gly
                245

<210> SEQ ID NO 10
<211> LENGTH: 280
<212> TYPE: PRT
<213> ORGANISM: Homo sapiens

<400> SEQUENCE: 10

Met Lys Tyr Leu Leu Pro Thr Ala Ala Gly Leu Leu Leu Leu Ala
1               5                   10                  15

Ala Gln Pro Ala Met Ala Asp Ile Val Met Thr Gln Ser Pro Ser Ser
                20                  25                  30

Leu Ser Ala Ser Val Gly Asp Arg Val Thr Ile Thr Cys Arg Ala Ser
            35                  40                  45

Arg Asp Ile Ser Asn Tyr Leu Asn Trp Tyr Gln Gln Lys Pro Gly Lys
50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Thr Tyr Tyr Cys Gln Gln
            100                 105                 110

Tyr Asp Asn Leu Pro Arg Leu Gly Lys Phe Gly Gly Gly Thr Lys Val
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys Ser Ala
225                 230                 235                 240

Arg Gln Ser Thr Pro Phe Val Cys Glu Tyr Gln Gly Gln Ser Ser Asp
                245                 250                 255

Leu Pro Gln Pro Pro Val Asn Ala Gly Gly Ser Gly Gly Gly Ser
            260                 265                 270

Gly Gly Gly Ser Glu Gly Gly Gly
            275                 280

<210> SEQ ID NO 11
<211> LENGTH: 7
<212> TYPE: PRT
<213> ORGANISM: artificial sequence
<220> FEATURE:
```

```
<223> OTHER INFORMATION: derived from CECR1_2

<400> SEQUENCE: 11

Ser Gln Val Phe Asn Ile Leu
1               5

<210> SEQ ID NO 12
<211> LENGTH: 10
<212> TYPE: PRT
<213> ORGANISM: Artificial Sequence
<220> FEATURE:
<223> OTHER INFORMATION: derived from CHI3L2

<400> SEQUENCE: 12

Ile Leu Gly Gln Gln Val Pro Tyr Ala Thr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: derived from CHI3L2

<400> SEQUENCE: 13

Leu Val Cys Tyr Tyr Thr Ser Trp Ser Gln Tyr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: derived from CHI3L1

<400> SEQUENCE: 14

Leu Leu Leu Thr Ala Gly Val Ser Ala Gly
1               5                   10

<210> SEQ ID NO 15
<211> LENGTH: 17
<212> TYPE: PRT
<213> ORGANISM: Artificial Sequence
<220> FEATURE:
<223> OTHER INFORMATION: derived from CHI3L1

<400> SEQUENCE: 15

Gly Pro Ser Ser Tyr Tyr Asn Val Glu Tyr Ala Val Gly Tyr Trp Ile
1               5                   10                  15

His

<210> SEQ ID NO 16
<211> LENGTH: 15
<212> TYPE: PRT
<213> ORGANISM: Artificial Sequence
<220> FEATURE:
<223> OTHER INFORMATION: derived from CHIT1

<400> SEQUENCE: 16

Val Gly Ala Pro Ala Thr Gly Ser Gly Thr Pro Gly Pro Phe Thr
1               5                   10                  15

<210> SEQ ID NO 17
<211> LENGTH: 13
<212> TYPE: PRT
<213> ORGANISM: Artificial Sequence
```

```
<220> FEATURE:
<223> OTHER INFORMATION: derived from CH1T1

<400> SEQUENCE: 17

Asp Asn Gln Trp Val Gly Phe Asp Asp Val Glu Ser Phe
1               5                   10

<210> SEQ ID NO 18
<211> LENGTH: 9
<212> TYPE: PRT
<213> ORGANISM: Artificial Sequence
<220> FEATURE:
<223> OTHER INFORMATION: defrived from FHR1

<400> SEQUENCE: 18

Asn His Gly Ile Leu Tyr Asp Glu Glu
1               5

<210> SEQ ID NO 19
<211> LENGTH: 15
<212> TYPE: PRT
<213> ORGANISM: Artificial Sequence
<220> FEATURE:
<223> OTHER INFORMATION: derived from IGKC

<400> SEQUENCE: 19

Ser Gly Thr Ala Ser Val Val Cys Leu Leu Asn Asn Phe Tyr Pro
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: derived from LIZ1

<400> SEQUENCE: 20

Trp Glu Ser Gly Tyr Asn Thr
1               5

<210> SEQ ID NO 21
<211> LENGTH: 7
<212> TYPE: PRT
<213> ORGANISM: Artificial Sequence
<220> FEATURE:
<223> OTHER INFORMATION: derived from RELN

<400> SEQUENCE: 21

Val Ile Val Leu Leu Pro Gln
1               5
```